US009950976B1

(12) United States Patent
Keller

(10) Patent No.: US 9,950,976 B1
(45) Date of Patent: Apr. 24, 2018

(54) CANNABIDIOL EXTRACTION AND CONVERSION PROCESS

(71) Applicant: CLS Labs, Inc., Miami, FL (US)

(72) Inventor: Raymond M. Keller, Naples, FL (US)

(73) Assignee: CLS LABS, Inc., Miami, FL (US)

( * ) Notice: Subject to any disclaimer, the term of this patent is extended or adjusted under 35 U.S.C. 154(b) by 0 days.

(21) Appl. No.: 14/923,617

(22) Filed: Oct. 27, 2015

(51) Int. Cl.
C07C 37/00 (2006.01)
B01D 11/02 (2006.01)

(52) U.S. Cl.
CPC .......... C07C 37/004 (2013.01); B01D 11/028 (2013.01); B01D 11/0273 (2013.01)

(58) Field of Classification Search
CPC .................................................. C07C 37/004
See application file for complete search history.

(56) References Cited

U.S. PATENT DOCUMENTS

| 6,403,126 B1* | 6/2002 | Webster | A61K 36/185 424/725 |
| 7,399,872 B2* | 7/2008 | Webster | C07D 311/80 549/390 |
| 2002/0086438 A1* | 7/2002 | Elsohly | B01D 15/265 436/177 |
| 2003/0017216 A1* | 1/2003 | Schmidt | A61K 36/185 424/725 |
| 2004/0049059 A1* | 3/2004 | Mueller | A61K 31/35 549/390 |
| 2005/0266108 A1* | 12/2005 | Flockhart | C07D 311/80 424/774 |
| 2006/0167283 A1* | 7/2006 | Flockhart | C07C 37/70 549/390 |

* cited by examiner

Primary Examiner — Valerie Rodriguez-Garcia
(74) Attorney, Agent, or Firm — Malloy & Malloy, P.L.

(57) ABSTRACT

A cannabidiol extraction and conversion process includes an extraction process including a sizing unit wherein raw *Cannabis* plant material is reduced to a uniform size, a blending unit wherein an extraction solvent is blended together with the *Cannabis* plant material to form an initial extract, and a primary solvent exchange rotary evaporator unit wherein an exchange solvent is added to the initial extract, and a processed extract rich in cannabidiol is obtained. A conversion process includes a conversion rotary reflux unit wherein the processed extract is combined and processed with an acidic component, a separator unit wherein a solvent is added and a separator organic effluent is obtained, a secondary solvent exchange rotary evaporator unit wherein a further solvent is added, and a fractionation unit wherein the tetrahydrocannabinol obtained is separated into a plurality of functional fractions for selective blending.

11 Claims, 4 Drawing Sheets

CANNABIDIOL EXTRACTION AND CONVERSION PROCESS

BACKGROUND OF THE INVENTION

Field of the Invention

The present invention is directed to a process for the extraction of cannabidiol from any of a variety of plants of the genus *Cannabis*, including but not limited to industrial hemp varieties which have been specifically bred to substantially limit the amount of the psychoactive cannabinoid, tetrahydrocannabinol, produced therein. The present invention is further directed to a procedure for the conversion of cannabidiol, such as may be extracted in commercially viable amounts from industrial hemp, to tetrahydrocannabinol.

Description of the Related Art

Various attempts have been made to extract tetrahydrocannabinol and other cannabinoid constituents present in industrial hemp in order to isolate the psychoactive cannabinoid fractions therein. At least two of the known processes require operation under supercritical conditions which, in addition to being extremely expensive to construct and operate on a commercial scale, are complicated and considerably more dangerous to operate than processes operating closer to ambient conditions. Butane and carbon dioxide are known to have been utilized as extraction "fluids" in such supercritical processes.

A further disadvantage of butane as a supercritical extraction "fluid" lies in the fact that commercial grade butane includes amounts of mercaptan to provide for odor detection, as pure butane is odorless. As such, extracts obtained via this supercritical butane extraction process also comprise unwanted amounts of mercaptan as well.

Another process utilizes ethanol as an extraction fluid, however, less than pure ethanol is often utilized, i.e., denatured ethanol, thereby allowing harmful contaminants in the denatured ethanol to pass though to the extracted cannabinoid constituents.

One crude conversion process is known to exist which begins with an oily feedstock rich in Δ8-tetrahydrocannabinolic acid ("THCA") and isomers thereof. The THCA is spread onto parchment paper or a similar substrate, and is exposed to extreme heat, such as may be provided by industrial heaters, resulting in decarboxylation and formation of the psychoactive cannabinoid fraction, tetrahydrocannabinol. As will be appreciated, such a process is inefficient and difficult to control, thus resulting in end products having widely varying amounts of conversion product, i.e., tetrahydrocannabinol.

As such, it would be beneficial to provide a safe and economical process for the extraction of cannabinoid components from industrial hemp. It would be further advantageous to have a conversion process wherein an extraction component rich in cannabidiol is converted into a conversion product rich in tetrahydrocannabinol. A further benefit may be realized by providing a process for fractionation of a conversion product into a plurality of cannabinoid classes which may subsequently be recombined in predetermined amounts in order to mimic the cannabinoid profile in well known, but difficult and/or expensive to cultivate strains of *Cannabis* plants.

SUMMARY OF THE INVENTION

The present invention is directed to a cannabidiol extraction and conversion process. In at least one embodiment, a cannabidiol extraction process includes a sizing unit wherein an amount of raw *Cannabis* plant material is reduced to a uniform size in order to maximize the extraction efficiency therefrom upon contact with one or more extraction solvents.

A blending unit is provided in at least one embodiment of a cannabidiol extraction process in accordance with the present invention wherein a first solvent is blended together with the *Cannabis* plant material to form an initial extract. A primary filtration unit and/or an extraction adsorption unit are incorporating into at least one embodiment of a conversion process in order to remove unwanted plant matter and/or other unwanted extraction byproducts from the initial extract.

In accordance with one further embodiment of a cannabidiol extraction process in accordance with the present invention, a primary solvent exchange rotary evaporator unit wherein the initial extract is processed further with a second solvent, thereby forming a processed extract.

As noted above, the present invention further comprises a cannabidiol conversion process. In at least one embodiment, a cannabidiol conversion process comprises a conversion rotary reflux unit wherein a processed extract is processed with an acidic component to form a conversion reflux. A separator unit is provided in one embodiment to remove solvent from the conversion reflux and produce a separator organic effluent. A secondary solvent exchange rotary evaporator unit is employed in at least one embodiment to exchange remaining solvent from the separator organic effluent, resulting in an exchange reflux.

In at least one embodiment, a fractionation unit is employed to separate the exchange reflux into a plurality of cannabinoid classes or fractions, which may be subsequently recombined in predetermined amounts in order to mimic the cannabinoid profile in well known, but difficult and/or expensive to cultivate strains of *Cannabis* plants.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION

Figure 1A:
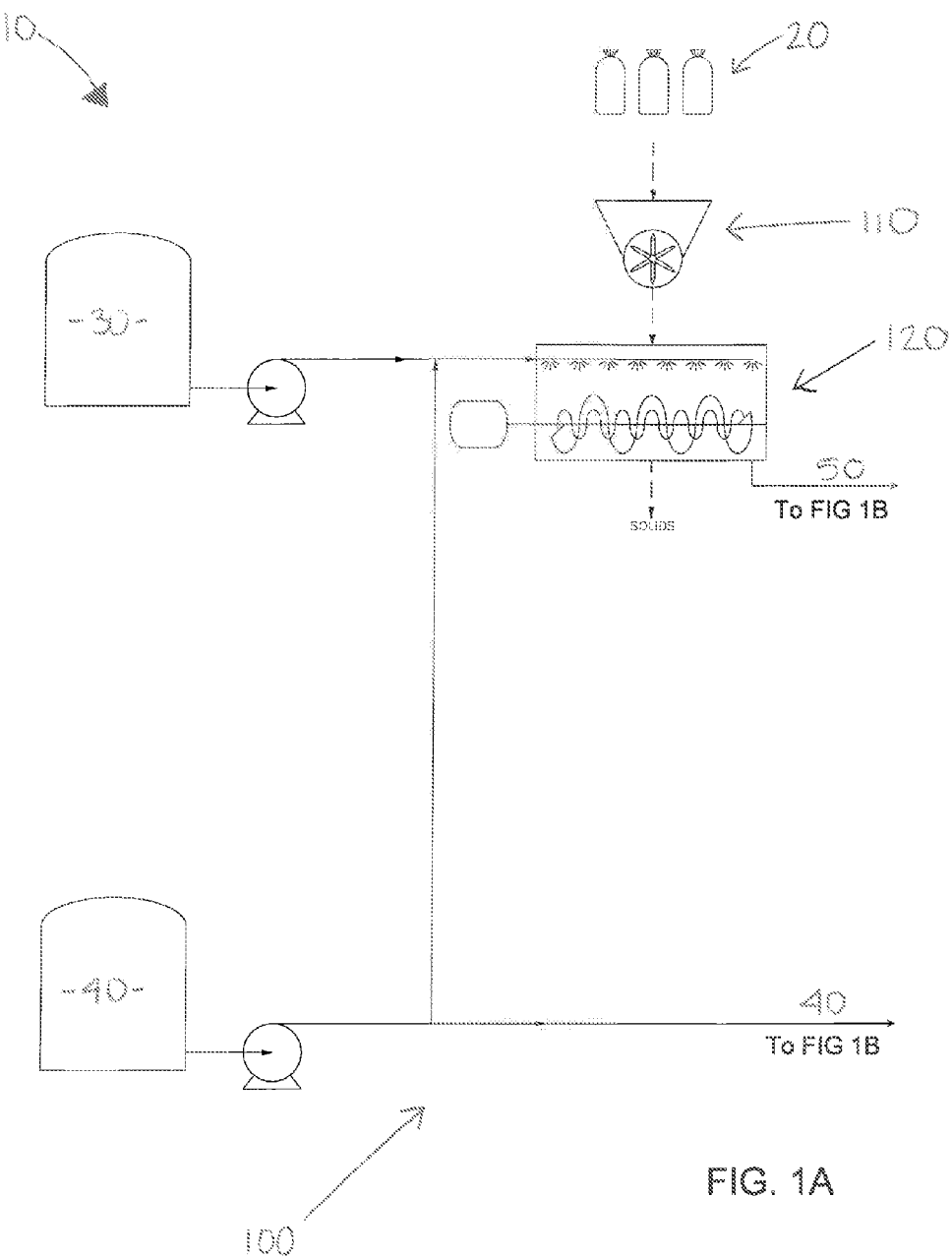
FIGS. 1A and 1B present a diagrammatic representation of one illustrative embodiment of an extraction process of a cannabidiol extraction and conversion process in accordance with the present invention.

The present invention is directed to a cannabidiol extraction and conversion process, as stated above. More in particular, in at least one embodiment of the present invention, cannabidiol is extracted from a plant of the genus *Cannabis*. In yet one further embodiment, the plant of the genus *Cannabis* comprises industrial hemp which has been specifically bred to substantially limit the amount of the psychoactive cannabinoid, tetrahydrocannabinol, produced therein, in favor of the non-psychoactive cannabinoid, cannabidiol.

In at least one embodiment, the raw *Cannabis* plant material is dried to minimize the amount of water present therein which may reduce the efficiency of the extraction process. The stems, stalks, and roots of the *Cannabis* plant are cut or chopped into small pieces prior to placement into an extraction vessel. The flowers, buds, and leaves of the *Cannabis* plant, in general, do not require any size reduction prior to the extraction process. In at least one embodiment, the stems, stalks, and roots of the *Cannabis* plant are cut or chopped into pieces having a maximum dimension of about one-quarter inch to about one-half inch. In one further embodiment, the raw *Cannabis* plant material is dried after being cut or chopped into small pieces, so as to facilitate the drying process.

The sized *Cannabis* plant material which, as used herein, includes the stems, stalks, and roots of the *Cannabis* plant which have been cut or chopped into pieces along with any flowers, buds, or leaves present, is placed into an extraction vessel and is substantially covered with a solvent. In one embodiment, the solvent comprises dichloromethane, i.e., $CH_2Cl_2$, and in at least one embodiment, the dichloromethane has a purity of about 95 percent.

The mixture of sized *Cannabis* plant material and dichloromethane is shaken or stirred during an initial extraction cycle until the solvent takes on color from the *Cannabis* plant material. Once the solvent has taken on color from the *Cannabis* plant material, the extraction solution is drained from the extraction vessel. The extraction cycle is repeated with fresh dichloromethane being used for each additional extraction cycle. In at least one embodiment, two additional extraction cycles are performed. The extraction solutions recovered from the extraction vessel from each of the extraction cycles are combined into a single vessel, and the remaining solid *Cannabis* plant material may be discarded.

The combined extraction solution is processed through activated carbon to adsorb solids and other unwanted components from the combined extraction solution. In at least one embodiment, granular activated carbon having an average size of about 35 to 40 micron, i.e., U.S. Mesh 400, is utilized. A contact time of the combined extraction solution with the granular activated carbon of about 20 to 45 minutes is utilized in accordance with one embodiment of the present invention.

After processing through activated carbon, in accordance with at least one embodiment of the present invention, an amount of combined extraction solution of about 20 to 50 liters is placed into a 100 liter rotary evaporator to remove excess dichloromethane. As will be appreciated by those of skill in the art, the volume of extraction solution and the volume of the evaporator can be scaled up, as needed, for large capacity production, such as is disclosed in Example 1 below with reference to the figures herein.

In at least one embodiment, the rotary evaporator operates under a slight vacuum in the range of about 400 to 600 millimeters of mercury ("mm HG"). In one further embodiment, the combined extraction solution in the rotary evaporator is maintained at a temperature in a range of about 40 to 50 degrees Celsius ("° C."), and in yet one further embodiment, the rotary evaporator is maintained at a temperature of about 43° C. The rotary evaporator, in accordance with one embodiment of the present invention, is operated at a speed in a range of about 100 to 200 revolutions per minute ("rpm").

During the rotary evaporation process, dichloromethane is removed and a concentrated extract remains. An amount of ethanol, i.e., $C_2H_5OH$, is added to the concentrated extract in the rotary evaporator. In one embodiment, the ethanol has a purity of about 100%. The ethanol and concentrated extract are allowed to blend together in the rotary evaporator at a speed of about 100 to 200 rpm, until a homogenous solution is obtained. In at least one embodiment, the amount of ethanol added is equal to about three times the amount of the concentrated extract remaining in the rotary evaporator following the rotary evaporation process.

Following the blending process, the ethanol extract is defatted via a wax coalescing process, and in one further embodiment, a filter is utilized to collect and remove coalesced fat from the ethanol extract, leaving a processed extract comprising cannabidiol in a range of about 60% to 80% by weight.

As noted above, the present invention further comprises a process for the conversion of cannabidiol to tetrahydrocannabinol. To begin, in at least one embodiment, an amount of defatted extract comprising cannabidiol in a range of about 60% to 80% by weight is placed into a reflux reaction vessel. One drop of concentrated sulfuric acid, i.e., 95% to 98% sulfuric acid, is added to the reflux reaction vessel per gram of defatted extract. The reflux reaction is carried out under a vacuum in a range of about 400 to 600 mm HG at a temperature in arrange of about 80° C., for a time of about 2 hours.

The refluxed extract is placed into a separator with water and dichloromethane. In at least one embodiment, the amount of water added to the separator is about twice the amount of the refluxed extract, and the amount of dichloromethane added is about equal to the amount of the refluxed extract.

The separator is shaken to thoroughly mix the aqueous and organic fractions, and the resulting mixture is allowed to stand for about 30 minutes to separate into layers. In at least one embodiment, the separator is vented to atmosphere. The aqueous layer is decanted from the separator and discarded.

The remaining organic extract is then rinsed in the separator with an amount of water equal to about twice the volume of the organic extract remaining, and an amount of one normal sodium hydroxide solution, i.e., 1N NaOH, is added. In at least one embodiment, the amount of 1N NaOH solution added is equal to the amount of concentrated sulfuric acid added during the extraction process. This mixture is agitated and the pH tested. Additional amounts of the 1N NaOH are added under agitation until the pH of the solution is about neutral, i.e., a pH of about 7.

Once the pH has been adjusted to about neutral, the solution is agitated further, vented, and is allowed to separate. The aqueous layer is once again decanted and discarded, and the remaining organic layer is rinsed with water in accordance with the foregoing procedure two additional times.

The rinsed organic extract is filtered through activated carbon to remove residual water. In at least one embodiment, the carbon filtration is performed under vacuum.

After carbon filtration, the organic extract is filtered to about 2 microns and is once again transferred into a rotary evaporator to remove dichloromethane. In at least one embodiment, an amount of ethanol is added to the oily extract in a ratio of about three parts ethanol to one part of oily extract.

A final step, in at least one embodiment, is to dry the ethanol/oil mixture in the rotary evaporator to remove any dichloromethane which remains entrapped therein, and the finished product is packaged for further use.

In accordance with at least one embodiment of the present invention, a defatted extract comprising cannabidiol in a range of about 60% to 80% by weight is converted into an ethanol/oil mixture comprising tetrahydrocannabinol in a range of about 60% to 80% by weight.

EXAMPLE I: EXTRACTION PROCESS

As stated above, the present invention is directed to a cannabidiol extraction and conversion process generally as shown as at 10 throughout the figures. More in particular, FIGS. 1A and 1B present one illustrative embodiment of a cannabidiol extraction process 100, while FIGS. 2A and 2B present one illustrative embodiment of a cannabidiol conversion process 200.

Figure 1B:
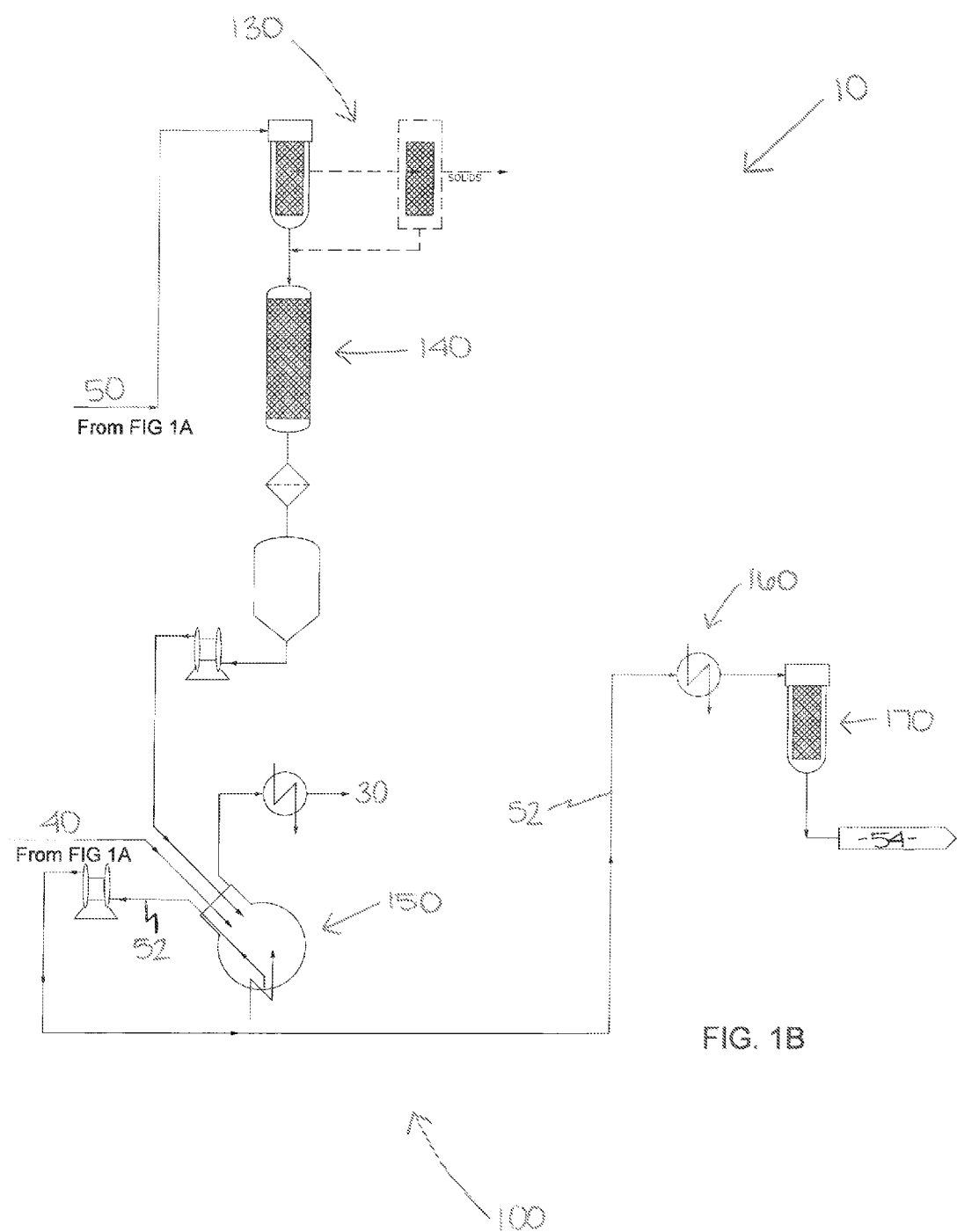
Figure 2A:
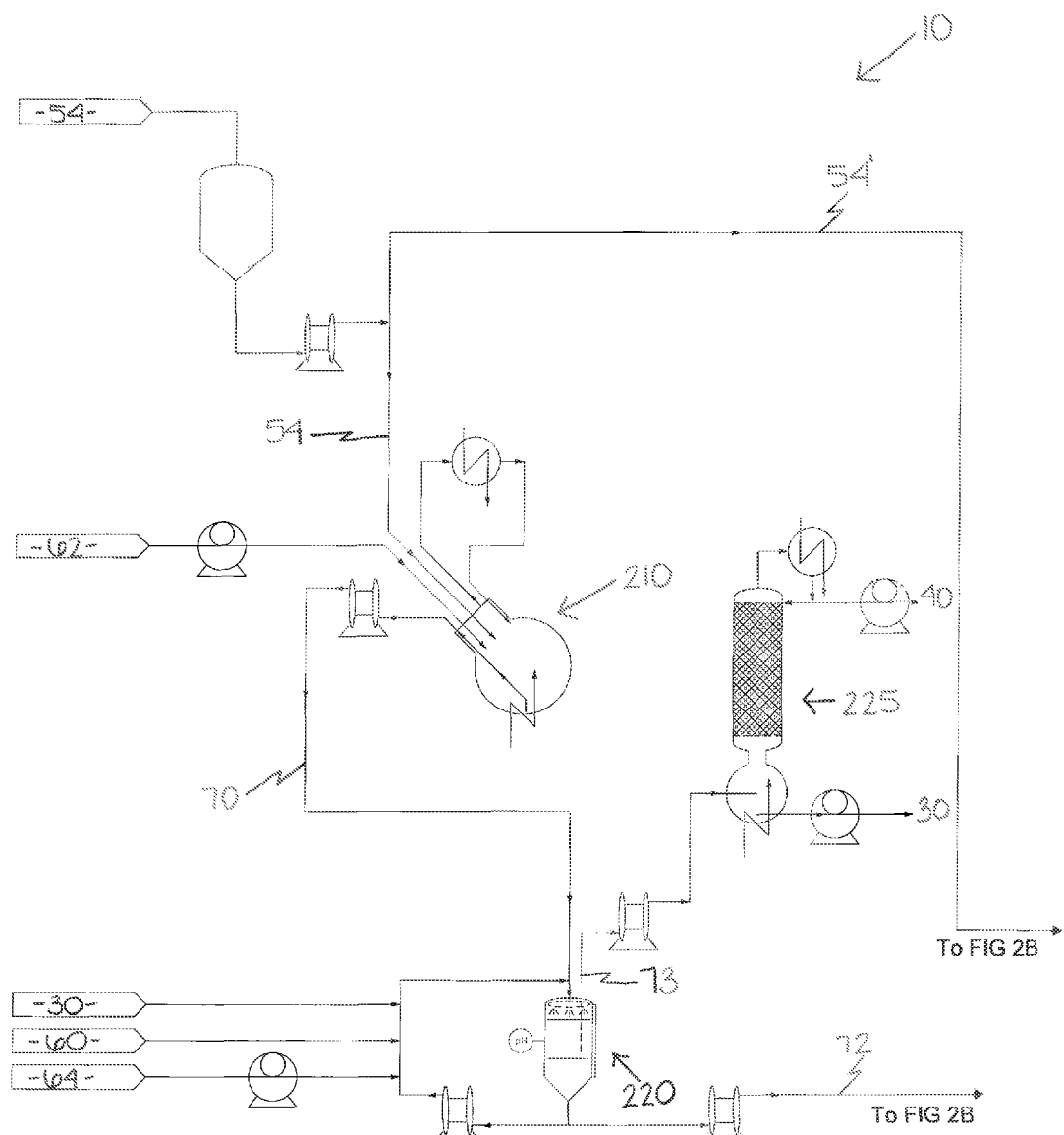
FIGS. 2A and 2B present a diagrammatic representation of one illustrative embodiment of a conversion process of a cannabidiol extraction and conversion process in accordance with the present invention.
Figure 2B:
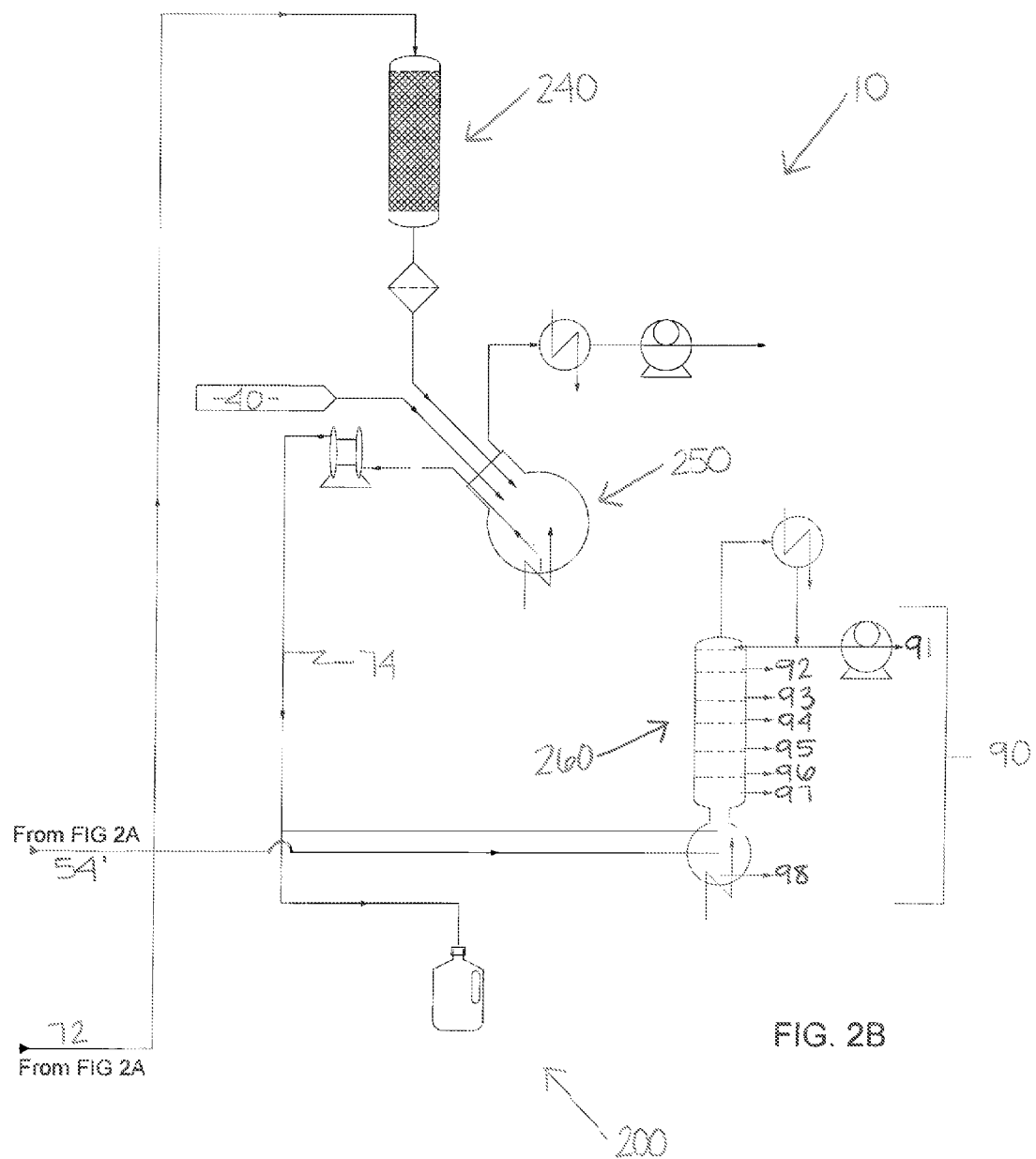

Turning first to the illustrative embodiment of a cannabidiol extraction process 100 as shown in FIGS. 1A and 1B, the process begins with an amount of raw materials, namely, raw *Cannabis* plant material 20. As before, in at least one embodiment, the raw *Cannabis* plant material 20 utilized in accordance with the present invention comprises industrial hemp varieties specifically bred to substantially limit the amount of tetrahydrocannabinol produced therein.

The extraction process further comprises at least one extraction solvent. In at least one embodiment, such as shown in FIG. 1A, an extraction process 100 in accordance with the present invention comprises a plurality of extraction solvents, namely, extraction solvent A 30 and extraction solvent B 40. In accordance with at least one embodiment of the present invention, extraction solvent A 30 comprises dichloromethane, i.e., $CH_4Cl_2$. In one further embodiment of an extraction process 100 in accordance with the present invention extraction solvent B 40 comprises ethanol, i.e., $C_2H_5OH$.

Looking further to the illustrative embodiment of FIG. 1A, the extraction process 100 comprises a sizing unit 110 which is utilized to cut, chop, etc., the raw *Cannabis* plant material 20 into an appropriate size for extraction of cannabidiol therefrom. In at least one embodiment, a sizing unit 110 reduces the raw *Cannabis* plant material 20 to pieces having a uniform maximum dimension of about one-quarter inch to one-half inch.

Following the sizing unit 110, the sized *Cannabis* plant material 20 is transferred to a blending unit 120. It is in blending unit 120 that the primary extraction occurs, and as such, amounts of extraction solvent A 30 and/or amounts of extraction solvent B 40 are introduced into blending unit 120 with a corresponding amount of sized *Cannabis* plant material 20. In at least one embodiment, the blending process utilizes solvent A 30 comprising dichloromethane, and is carried out at ambient temperature and pressure for a period of about 20 minutes, per batch, at a speed of about 30 rpm. In one further embodiment, solvent A 30 comprises dichloromethane having a purity of about 95 percent.

As further shown in the illustrative embodiment of FIG. 1A, following the primary extraction process in the blending unit 120, solid plant material is discharged, and may be discarded, and an initial extract 50 is retained for further processing.

Turning next to FIG. 1B, the initial extract 50 from blending unit 120 is directed through a primary filtration unit 130. As will be appreciated by those with skill in the art, primary filtration unit 130 may include an appropriately sized bag or screen type filter so as to remove any solid particulate plant material remaining in the initial extract 50.

In at least one embodiment, primary filtration unit 130 further comprises a bag filter press for collection and removal of solid particulate matter from the initial extract 50.

With further reference to the illustrative embodiment of FIG. 1B, the present extraction process 100 further comprises an extraction adsorption unit 140. In at least one embodiment, an extraction adsorption unit 140 comprises an amount of an appropriately sized granular activated carbon material which is selected to remove specific unwanted components from initial extract 50. A contact time of about 20 to 30 minutes for the initial extract 50 in the extraction adsorption unit 140 is utilized in at least one embodiment of the present invention.

Following the extraction adsorption unit 140, the initial extract 50 is introduced into a primary solvent exchange rotary evaporator unit 150. As shown in the illustrative embodiment of FIG. 1B, an amount of solvent B 40 is also fed into the primary solvent exchange rotary evaporator unit 150. Once again, in at least one embodiment of the present extraction process 100, solvent B 40 comprises ethanol having a purity of about 100%. In one further embodiment, the amount of solvent B 40 comprising 100% ethanol added to the primary solvent exchange rotary evaporator unit 150 is about equal to the amount of initial extract 50 added thereto.

The primary solvent exchange rotary evaporator unit 150 in accordance with at least one embodiment of the present invention is operated at a temperature of about 40 to 60° C. under a vacuum of about 400 to 600 mm Hg. In accordance with at least one further embodiment, the primary solvent exchange rotary evaporator unit 150 operates at a speed in a range of about 100 to 200 rpm. In yet one further embodiment, the initial extract 50 is processed in the primary solvent exchange rotary evaporator unit 150 with solvent B 40 for a period of time in a range of about 2 to 3 hours.

An evaporated extract 52 is obtained from the primary solvent exchange rotary evaporator unit 150. Further, an amount of solvent A 30 may be recovered via a condenser unit and recycled to the solvent A 30 storage tank. The resultant evaporated extract 52 is relatively high in fatty content and as such, in at least one embodiment, the evaporated extract 52 is processed through a wax coalescing unit 160 so as to "defat" the evaporated extract 52.

In one further embodiment, a secondary extraction filtration unit 170 is employed following a wax coalescing unit 160 to collect waxes and/or fats which drop from solution in the wax coalescing unit 160, thereby resulting in an end product of one embodiment of the extraction process 100 in accordance with the present invention, namely, a processed extract 54. As will be appreciated by those of skill in the art, processed extract 54 will be relatively high in cannabidiol content. More in particular, a processed extract 54 obtained via an extraction process 100 in accordance with at least one embodiment of the present invention will comprise cannabidiol in amounts in a range of about 60% to 80% by weight.

EXAMPLE II: CONVERSION PROCESS

Turning next to the illustrative embodiment presented in FIGS. 2A and 2B, a conversion process 200 in accordance with the present cannabidiol extraction and conversion process 10 is presented. As shown in the illustrative embodiment of FIG. 2A, a processed extract 54, such as may be obtained from extraction process 100 in accordance with the present invention, is a primary feedstock to a conversion process 200. More in particular, a processed extract 54 is introduced into a conversion rotary reflux unit 210 along with the amount of acidic component 62. More in particular, in at least one embodiment, acidic component 62 comprises sulfuric acid, and in one further embodiment, acidic component 62 comprises concentrated sulfuric acid, i.e., sulfuric acid at a concentration of about 95% to 98%. The acidic component 62 comprising concentrated sulfuric acid is added to a conversion rotary reflux unit 210 in an amount in a range of about 2% to 3% of the weight of the processed extract 54, in accordance with at least one embodiment of the present conversion process 200.

A conversion rotary reflux unit 210 in one embodiment is operated at a temperature of about 40 to 60° C., and under a vacuum in a range of about 400 to 600 mm Hg. In accordance with at least one embodiment, the conversion rotary reflux unit 210 operates at a speed of about 100 to 200 rpm. In yet one further embodiment, the processed extract 54 is processed in the conversion rotary reflux unit 210 for a period of about 2 to 3 hours.

Following the conversion rotary reflux unit 210, a conversion reflux 70 is introduced into a separator unit 220. As shown in the illustrative embodiment of FIG. 2A, an amount of extraction solvent A 30 is introduced into separator unit 220 with the conversion reflux 70. As before, in at least one embodiment, solvent A 30 comprises dichloromethane, and in one further embodiment, solvent A 30 comprises dichloromethane having a purity of about 95 percent. In addition, in accordance with one embodiment of the present conversion process 200, amounts of deionized water 60 and a basic component 64 are also added to separator unit 220 with the conversion reflux 70 and solvent A 30.

In accordance with one embodiment of the present conversion process 200, the amount of solvent A 30 added to the separator unit 220 is about equal to the volume of conversion reflux 70 added thereto, and the amount of deionized water 60 added to the separator unit 220 is equal to about two times the volume of conversion reflux 70. The basic component 64 comprises 1N NaOH in at least one embodiment, and is added in amounts sufficient to adjust the pH of the mixture of the conversion reflux 70, solvent A 30, and deionized water 60 in separator unit 220 to approximately neutral. Separator unit 220 operates at ambient temperature and pressure in accordance with at least one embodiment of the present conversion process 200.

As shown in the illustrative embodiment of FIG. 2A, a separator organic effluent 72 is obtained from separator unit 220. Further, a solvent layer 73, consisting primarily of solvent A 30 and/or solvent B 40 from separator unit 220, is directed to a solvent distillation unit 225 for separation and return to the respective solvent storage tanks for use in the extraction process 100.

Turning next to the illustrative embodiment of FIG. 2B, the separator organic effluent 72 is initially processed through a conversion adsorption unit 240. As with extraction adsorption unit 140, in at least one embodiment, a conversion adsorption unit 240 in accordance with the present invention comprises an amount of granular activated carbon to remove select unwanted components from the separator organic effluent 72. In at least one embodiment, a U.S. mesh 400 activated carbon in utilized in conversion adsorption unit 240. A contact time of about 20 to 45 minutes is provided for the separator organic effluent 72 in the conversion adsorption unit 240 in accordance with at least one embodiment of the present invention, and in at least one further embodiment, a contact time of about 30 to 45 minutes is provided.

Following the conversion adsorption unit 240, the separator organic effluent 72 is introduced into a secondary solvent exchange rotary evaporator unit 250. As further shown in the illustrative embodiment of FIG. 2B, an amount of solvent B 40 is also introduced into the secondary solvent exchange rotary evaporator unit 250. Solvent B 40 in at least one embodiment, as before, comprises ethanol, and in one further embodiment, solvent B 40 comprises ethanol having a concentration of about 100%. The amount of solvent B 40 added to secondary solvent exchange rotary evaporator unit 250, in one embodiment, is in a range of about one-half the volume of separator organic effluent 72 to about twice the volume of separator organic effluent 72. In at least one further embodiment, the amount of solvent B 40 added to the secondary solvent exchange rotary evaporator unit 250 is about equal to the volume of separator organic effluent 72.

In accordance with at least one embodiment of the present conversion process 200, a secondary solvent exchange rotary evaporator unit 250 is operated at a temperature of about 40 to 60° C., and under a vacuum in a range of about 400 to 600 mm Hg. In accordance with one further embodiment, a secondary solvent exchange rotary evaporator unit 250 is operated at a speed of about 100 to 200 rpm. In yet one further embodiment, the separator organic effluent 72 is processed in the secondary solvent exchange rotary evaporator unit 250 with solvent B 40 for a period of time in a range of about 1 to 4 hours, and in one further embodiment, the separator organic effluent 72 is processed in the secondary solvent exchange rotary evaporator unit 250 for about 2 hours.

After processing via the secondary solvent exchange rotary evaporator unit 250, an exchange reflux 74 is obtained from the secondary solvent exchange rotary evaporator unit 250. In accordance with at least one embodiment of the present invention, an exchange reflux 74 comprises about 60% to 80% tetrahydrocannabinol by weight.

Similar to primary solvent exchange rotary evaporator unit 150, in at least one embodiment of the present invention, a condenser is employed in combination with the secondary solvent exchange rotary evaporator unit 250 in order to recover an amount of solvent A 30 for return to solvent A 30 storage tank for further use in an extraction process 100 in accordance with the present invention.

The final step in accordance with at least one embodiment of a conversion process 200 of the present invention comprises processing an exchange reflux 74 through a fractionation unit 260. In at least one embodiment, the fractionation unit 260 separates the exchange reflux 74 into a plurality of functional fractions or classes which collectively define a conversion product 90. In accordance with at least one embodiment, the fractionation unit 260 separates the exchange reflux 74 into eight functional fractions or classes, namely, a cannabinol ("CBN") fraction 91, a tetrahydrocannabinol ("THC") fraction 92, a cannabigerol ("CBG") fraction 93, a cannabidiol ("CBD") fraction 94, a cannabichromene ("CBC") fraction 95, a cannabichromanone ("CBCN") fraction 96, a cannabifuran ("CBF") fraction 97, and a cannabielsoin ("CBE") fraction 98.

As such, the conversion product 90 in accordance with the present invention comprises functional fractions which may be selectively recombined, such as, by way of example, via blending either alone or in combination with inert carrier agents, in a manner that replicates the overall cannabinoid profile in various strains of specially grown *Cannabis* plants, and in at least one embodiment, to replicate the overall tetrahydrocannabinol profile of *Cannabis* plants exhibiting the greatest psychoactive properties.

Further, the conversion product 90 in accordance with the present invention comprises tetrahydrocannabinol which may administered via any of a number of delivery mechanisms including, at least, personal electronic vaporizing devices, more commonly known as e-cigarettes.

With reference once again to the illustrative embodiment of FIGS. 2A and 2B, and in accordance with at least one alternative embodiment of the present invention, a processed extract 54' obtained from extraction process 100 is processed directly via fractionation unit 260, bypassing the conversion rotary reflux unit 210, separator unit 220, conversion adsorption unit 240, and secondary solvent exchange unit 250. In this alternative embodiment, the fractionation unit 260 again separates the tetrahydrocannabinol and other target analytes present in the processed extract 54', albeit in lesser amounts than in exchange reflux 74, into a plurality of functional fractions which, once again, collectively define a conversion product 90. As before, the fractionation unit 260 separates the processed extract 54' into eight functional fractions, namely, a cannabinol ("CBN") fraction 91, a tetrahydrocannabinol ("THC") fraction 92, a cannabigerol ("CBG") fraction 93, a cannabidiol ("CBD") fraction 94, a cannabichromene ("CBC") fraction 95, a cannabichromanone ("CBCN") fraction 96, a cannabifuran ("CBF") fraction 97, and a cannabielsoin ("CBE") fraction 98.

Also as before, the conversion product 90 in accordance with this alternative embodiment of the present invention comprises functional fractions which may be selectively recombined in a manner that replicates the overall cannabinoid profile in various strains of specially grown *Cannabis* plants.

Of course, it will be appreciated by those of skill in the art that the foregoing extraction process 100 and conversion process 200 may be readily scaled up or down in order to increase and/or decrease throughput such as conditions may require. In at least one embodiment, the present cannabidiol extraction and conversion process 10 is sized to accommodate a feedstock input of about 115 kilograms, or approximately 250 pounds, of raw *Cannabis* plant material 20 per eight hour shift, which will produce an amount of about 35 to 45 kilograms of conversion product 90 which, once again, comprises about 60% to 80% tetrahydrocannabinol by weight.

Since many modifications, variations and changes in detail can be made to the described embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A cannabidiol extraction process including:
   sizing an amount of raw *Cannabis* plant material in a sizing unit wherein the amount of raw *Cannabis* plant material is reduced to a uniform size,
   blending an amount of dichloromethane having a purity of about ninety-five percent together with the amount of *Cannabis* plant material to form an initial extract,
   filtering the initial extract in a primary filtration unit,
   contacting the initial extract, after filtering the initial extract through the primary filtration unit, with activated carbon in an extraction adsorption unit,
   removing dichloromethane from the initial extract, after contacting the initial extract with activated carbon in the extraction adsorption unit, in a primary solvent exchange rotary evaporator unit,
   adding an amount of ethanol having a purity of about one hundred percent to the initial extract remaining in the primary solvent exchange rotary evaporator unit after at least partially removing dichloromethane, thereby producing an evaporated extract comprising cannabidiol in ethanol and dichloromethane, the evaporated extract comprising about sixty percent to about eighty percent cannabidiol by weight.

2. The cannabidiol extraction process as recited in claim 1 wherein the amount of raw *Cannabis* plant material is about 115 kilograms per day.

3. The cannabidiol extraction process as recited in claim 2 wherein dichloromethane is added to the raw *Cannabis* plant material in the blending unit in an amount of about three to four kilograms of dichloromethane per kilogram of raw *Cannabis* plant material.

4. The cannabidiol extraction process as recited in claim 1 further comprising processing the evaporated extract through a wax coalescing unit to coalesce waxes and fats present in the evaporated extract.

5. The cannabidiol extraction process as recited in claim 4 further comprising filtering the evaporated extract, after processing the evaporated extract through the wax coalescing unit, through a secondary filtration unit to remove coalesced waxes and fats to produce a processed extract.

6. A cannabidiol conversion process comprising:
   mixing an amount of concentrated sulfuric acid with an amount of a processed extract, the processed extract comprises cannabidiol in ethanol and dichloromethane, the processed extract comprising cannabidiol in a range of about sixty percent to about eighty percent by weight, in a conversion rotary reflux unit and refluxing therein to obtain a conversion reflux,
   combining an amount of dichloromethane with the conversion reflux in a separator unit, a solvent layer consisting primarily of dichloromethane and ethanol is removed from the separator unit, and a separator organic effluent remains therein,
   combining the separator organic effluent with an amount of ethanol in a secondary solvent exchange rotary evaporator unit wherein dichloromethane and ethanol are at least partially evaporated off to produce an exchange reflux which comprises tetrahydrocannabinol in ethanol and dichloromethane, the exchange reflux comprising about sixty percent to about eighty percent tetrahydrocannabinol by weight, and
   separating the exchange reflux into a plurality of cannabinoid fractions in a fractionation unit.

7. The cannabidiol conversion process as recited in claim 6 wherein the concentrated sulfuric acid has a concentration of about 95 percent to about 98 percent.

8. The cannabidiol conversion process as recited in claim 7 wherein the amount of concentrated sulfuric acid added to the processed extract is in a range of about two percent to three percent by weight of the amount of processed extract.

9. The cannabidiol conversion process as recited in claim 6 wherein the dichloromethane has a purity of about ninety-five percent.

10. The cannabidiol conversion process as recited in claim 9 wherein the dichloromethane is added to the conversion reflux in an amount of about one kilogram of dichloromethane per kilogram of the conversion reflux.

11. The cannabidiol conversion process as recited in claim 6 further comprising contacting the separator organic effluent obtained from the separator unit with activated carbon in a conversion adsorption unit prior to combining the separator organic effluent with ethanol in the secondary solvent exchange rotary evaporator unit.

\* \* \* \* \*